Figure 1:
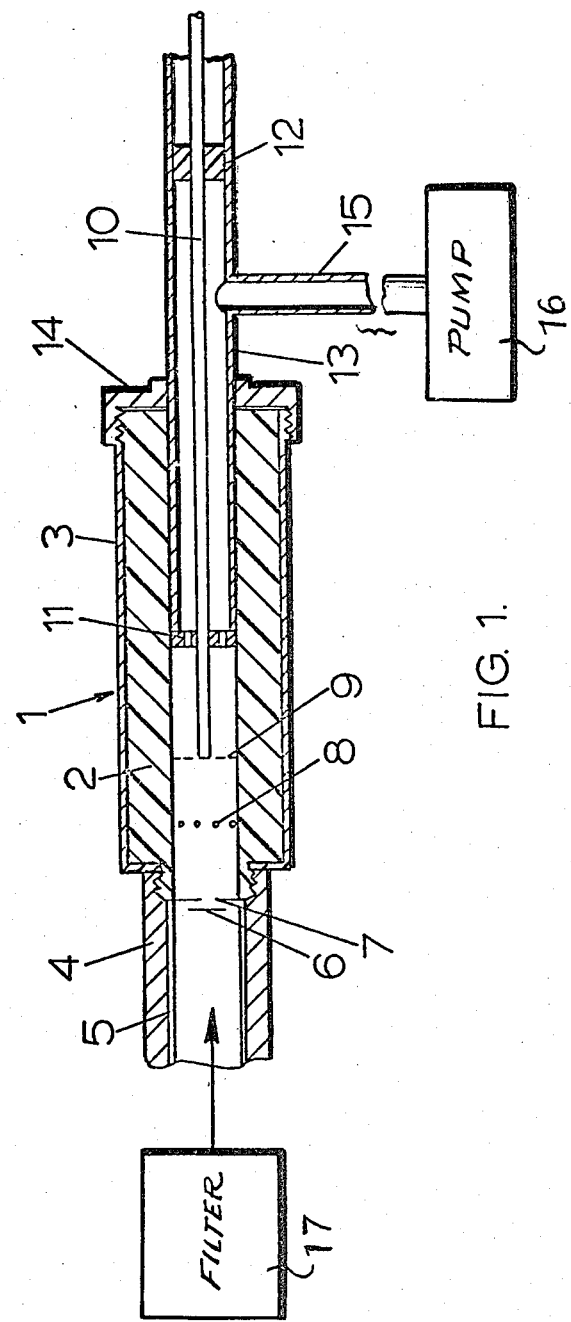

United States Patent [19]

Blyth

[11] 4,368,388
[45] Jan. 11, 1983

[54] DETECTION OF POLAR VAPORS

[75] Inventor: David A. Blyth, Salisbury, England

[73] Assignee: The Secretary of State for Defence in Her Britannic Majesty's Government of the United Kingdom of Great Britain and Northern Ireland, London, England

[21] Appl. No.: 97,930

[22] Filed: Nov. 15, 1979

Related U.S. Application Data

[62] Division of Ser. No. 752,828, Dec. 14, 1976, abandoned.

[30] Foreign Application Priority Data

Dec. 15, 1975 [GB] United Kingdom ............... 51362/75

[51] Int. Cl.³ ...................... H01J 49/00; H01J 49/22; H01J 49/42
[52] U.S. Cl. ........................ 250/283; 73/19; 73/23; 250/288; 250/294; 250/296; 250/287; 422/98
[58] Field of Search ............. 23/254 E, 255 E, 232 E; 250/281, 282, 283, 287, 288, 294, 296, 380, 381, 382, 384; 73/19, 23; 422/98

[56] References Cited

U.S. PATENT DOCUMENTS

| | | | |
|---|---|---|---|
| 2,810,075 | 10/1957 | Hall et al. | 250/290 |
| 3,211,996 | 10/1965 | Fox et al. | 250/287 |
| 3,400,264 | 9/1968 | Dull | 73/23 |
| 3,417,238 | 12/1968 | Hartmann | 250/384 |
| 3,522,425 | 8/1970 | Rich | 250/281 |
| 3,555,272 | 1/1971 | Munsom et al. | 250/288 |
| 3,621,240 | 11/1971 | Cohen et al. | 250/287 |
| 3,639,757 | 2/1972 | Caroll et al. | 250/288 |
| 3,699,333 | 10/1972 | Cohen et al. | 250/287 |
| 4,041,376 | 8/1977 | Furuto et al. | 250/384 |
| 4,053,776 | 10/1977 | Hertzberg et al. | 250/384 |

FOREIGN PATENT DOCUMENTS

| | | | |
|---|---|---|---|
| 1105604 | 3/1968 | United Kingdom | 250/283 |
| 1131932 | 10/1968 | United Kingdom | 250/384 |
| 1161190 | 8/1969 | United Kingdom | 250/283 |
| 1233915 | 6/1971 | United Kingdom | 250/283 |
| 1400333 | 7/1975 | United Kingdom | 250/283 |

Primary Examiner—Teddy S. Gron
Attorney, Agent, or Firm—Cushman, Darby & Cushman

[57] ABSTRACT

The invention provides an improved apparatus for the detection of polar vapors in a gas which avoids the need for liquid reagents and requires little maintenance. In its simplest form the apparatus comprises a body member defining a passage through which a gas stream may be caused to pass; an ionizing source for ionizing the gas stream; and a collector electrode positioned in the passage downstream of the ionizing source for collecting ions carried by the gas stream. Improved performance can be obtained by the provision of means for selectively removing uncombined gas ions from the gas stream between the ionizing source and the collector electrode while permitting ion clusters formed on polar molecules to remain therein.

19 Claims, 2 Drawing Figures

DETECTION OF POLAR VAPORS

This is a division of application Ser. No. 752,828 filed Dec. 14, 1976, now abandoned.

This invention relates to the detection of polar vapours in a gaseous atmosphere, for example polar vapours which may be present as pollutants in the atmosphere. The invention thus has application, for example, to the continuous monitoring of the atmosphere in an industrial environment where there is a risk of escape of hazardous or toxic polar vapours into the atmosphere.

Detectors which are currently available generally employ liquid reagents, which renders them inconvenient to use and necessitates periodic replacement of the reagents. There is thus a need for a detector which is capable of operation with little or no maintenance and without the use of liquid reagents.

According to the present invention, apparatus for the detection of a polar vapour in a gas comprises a body member having a passage through which a gas stream may be made to pass an ionising source for ionising the gas sample; and a collector electrode positioned in the passage downstream of the ionising source for collecting ions carried by the gas stream.

An explanation of the operation of the invention is thought to be as follows, although it should be understood that the invention is in no way to be limited thereby. The invention depends for its operation upon the ionisation of gas flowing through the passage past the ionising source. In the absence of any further influence, the concentration of ions in the gas downstream of the ionising source would decrease with distance as a result of re-combination and diffusion to the passage walls. If a polar vapour is present in the gas, it is believed that this results in the formation of ion clusters on the polar molecule. The ion clusters, by virtue of their greater mass, will have lower mobility than the gas ions, and hence the rate of loss of such ion clusters by re-combination and diffusion will be less than that of the gas ions. The ion current collected by an electrode placed in the gas passage downstream of the ionising source will thus be increased when a polar vapour is present in the sampled gas.

The device is therefore sensitive to polar vapours present in the atmosphere but, although a water molecule is polar, atmospheric water and changes in atmospheric humidity are not readily sensed by the device. This is probably due to the fact that in practice there will normally be sufficient water molecules present in the atmosphere to saturate the response of the device to water vapour.

The sensitivity to specific polar vapours of a simple device employing only an ionising source and a collector electrode can be very greatly improved, however, by use of some means for selectively removing gas ions from the gas stream whilst permitting the ion clusters formed on polar molecules to remain. This might be achieved, for example, by employing a magnetic field transverse to the gas passage, or alternatively by providing a long narrow gas passage between the ionising source and the collector electrode the ratio of length to mean width of the passage being at least 100 to 1 (so that the more mobile ions would diffuse to the walls). However, the preferred method by which this may most conveniently be achieved is by including means for applying, at a location between the ionising source and the collector electrode, an electrostatic field in which the lines of force are transverse to the direction of gas flow through the passage. The lighter, more mobile gas ions are influenced to a considerably greater extent by this field than are the heavier, less mobile ion clusters formed on the polar molecule. Hence, by an appropriate choice of gas flow rate, field strength and geometry, which can readily be determined by trial and error, it is possible to ensure that the majority of the ion clusters pass through the electrostatic field, whereas the majority of gas ions are removed. The ion current collected by the collector electrode will thus be almost entirely due to the presence of polar vapours in the sampled gas.

The preferred form of ionising source is a radioactive alpha-source. One particularly suitable source is americium 241, which has a particularly long half-life. This source is commercially available in foil form, which is relatively safe and convenient to use, and may readily be formed to the interior surface of the passage so as to surround the gas flow there-through.

When a radioactive ionising source is used, it is highly desirable to provide a baffle in the passage downstream thereof, to confine the area in which ionisation takes place, and to prevent radiation reaching the area of re-combination, for example downstream of the electrostatic field. Such a baffle should, of course, provide an effective barrier to radiation, whilst not unduly restricting the flow of sampled gas.

It has also been found preferable to include a dust filter to remove particulate matter in the gas entering the device. Filters which have been used with success have been made from a coarse-fibred polypropylene material, and alternatively from PTFE fibres. The provision of a filter, apart from its obvious function, tends also to result in smoothing out background noise, ie the random variations in the current output of the detector electrode are reduced in magnitude.

Whatever means is used to induce a flow of gas through the passage of the apparatus should be such as to ensure that as steady as possible a flow is obtained. Any variation in the gas flow rate of course results in a variation in the rate of arrival of ions at the collector electrode, and hence a variation in the current output. This kind of effect may explain in part why the provision of a filter assists in smoothing out background noise, possibly by helping to damp out minor fluctuations in the gas flow rate. Any form of pump used to induce a gas flow should preferably be connected to the downstream side of the apparatus, since polar vapours may otherwise tend to be adsorbed on the internal surfaces of the pump and thus not be detected at least without a delay. For similar reasons, the internal surface area over which sampled gas must flow prior to reaching the ionising source should be kept to a minimum so as to avoid adsorption effects. The use of non-adsorbent surface materials such as PTFE may assist in this respect.

The electrostatic field is conveniently applied via a grid of parallel wires extending in a transverse direction across the passage at a location between the ionising source and the collector electrode.

The collector electrode is conveniently constituted by a wire mesh screen extending across the passage. The ion current collected by the electrode may be measured by passing it through a high value resistor, and measuring the voltage developed across the resistor with an electrometer.

The passage should preferably be surrounded by a conducting material in order to provide screening from stray electrostatic fields which might otherwise adversely affect the operation of the device. Conveniently this screening is provided in the form of a strong metal component of the body member, which can then serve also to impart mechanical strength to the device.

Figure 2:
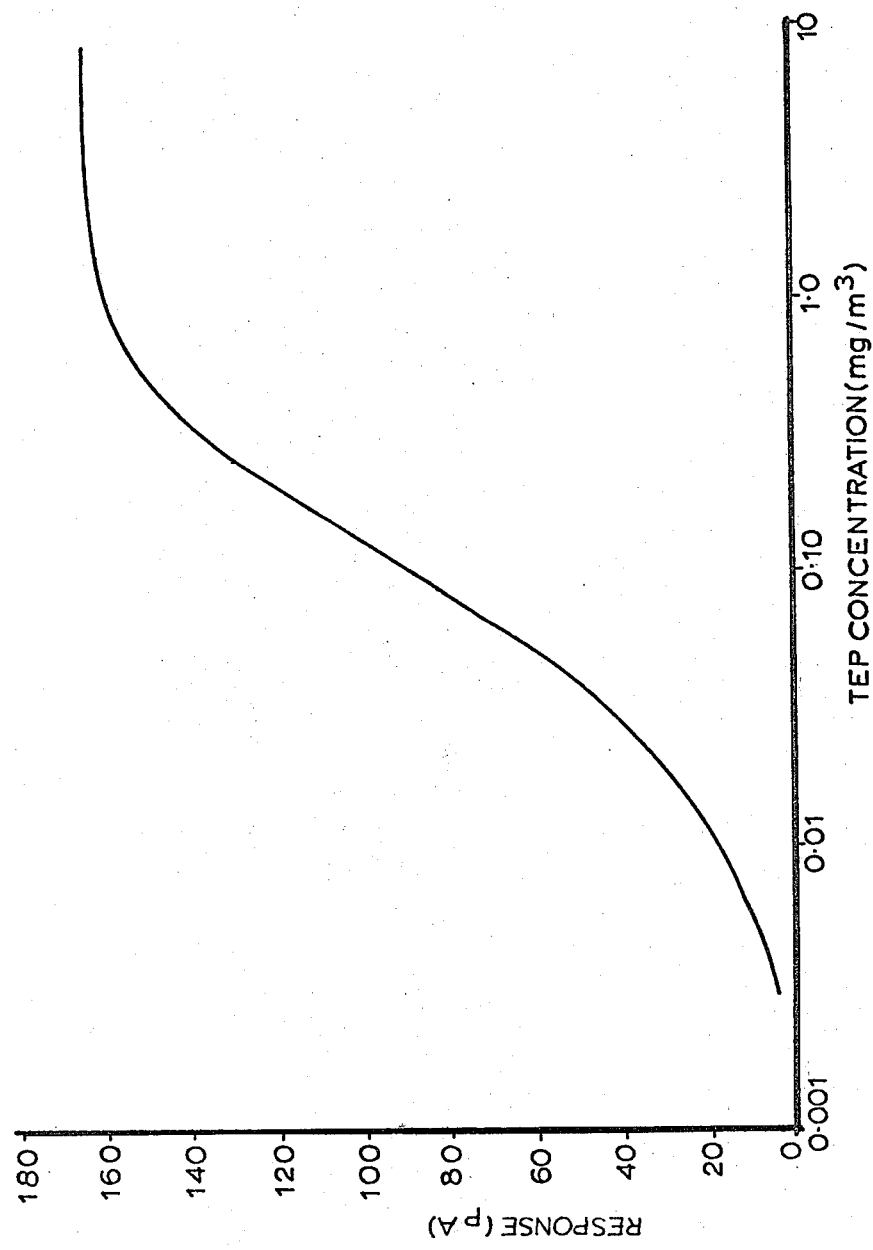

The invention will now be described, by way of example only, with reference to the accompanying drawings, in which FIG. 1 is a diagrammatic sectional elevation of an apparatus for the detection of polar vapours in the atmosphere, in accordance with the invention; and FIG. 2 is a calibration curve for the apparatus shown in FIG. 1, showing the response obtained when sampling varied concentrations of triethyl phosphate (TEP) in air.

As shown in FIG. 1, a device for the detection of polar vapours in the atmosphere comprises a cylindrical cell body generally indicated as 1 having a perspex inner portion 2 and a brass outer casing 3. A passage for air is provided by a concentric longitudinal bore passing from end to end through the inner portion 2.

The cell body 1 is provided at one end with a concentric screw-threaded projection, which engages with a corresponding screw threaded portion formed at one end of a cylindrical brass casing 4 containing an ionising source 5. The ionising source 5 is an americium 241 alpha-omitting source in the form of a thin foil, formed into a cylinder so as to conform to the inner surface of casing 4.

A baffle comprising a disc 6 and an annulus 7 of thin metal foil is interposed between body 1 and casing 3, to prevent radiation from source 5 reaching the passage formed within the body 1. The disc 6 is of greater diameter than the inner diameter of annulus 7, and is spaced apart therefrom by wire fingers (not shown) so as to permit the free passage of air therethrough.

Located within the passage formed in the body 1 is a grid 8 comprising a plurality of parallel wires extending across the passage. Alternate wires are electrically connected together.

Also located within the passage is a collector electrode 9 consisting of a wire mesh positioned transversely of the passage on the side of the grid 8 remote from the baffle, and spaced away from the passage wall. A screened electrical conductor 10 is connected to the collector electrode, and is supported in electrically insulating PTFE spacers 11, 12. The spacer 11 is perforated to allow air to pass therethrough. The spacer 12 provides a seal through which the conductor 10 passes to the exterior of the detector, whence it is connected through a high value resistor (not shown) to an electrometer (not shown).

A brass tube 13 is inserted into the downstream end of the body member 1, where it is located by the spacer 11, and an integral brass nut 14 engaging a screw thread on the exterior of casing 3. The tube 13 is sealed at its downstream end by the spacer 12, and has a side branch 15 which provides a connection for a pump 16. The pump should be such as to draw air through the device at as steady as possible a rate.

A dust filter 17 is provided upstream of the ionising source 5. The filter material may be, for example, a coarse-fibred polypropylene material marketed under the trade name "Bondina", or alternatively PTFE fibres may be used.

In use, air is drawn through the device by the pump, and is ionised as it passes through the radioactive source 5. One set of wires of the grid 8 is earthed, while the other set is maintained at a raised electrical potential, so as to create an electrostatic field transverse of the air flow direction. The collecting electrode 9 is held at an electrical potential difference from that of the ionising foil. An electrometer is connected, through a high-value resistor and the conductor 10, to the collector electrode 9, so that the electrometer reading provides an indication of the ion current collected.

A simple trial and error process may be employed to determine the optimum relative positions of the source 5, grid 8 and electrode 9 to give the maximum change in ion current for the introduction of a given concentration of a particular polar vapour. In practice it is found that the time of travel of the ions between the source 5 and collector electrode 9 is critical, thus fixing the optimum distance between them for a given air flow rate. The optimum position of the grid 8 was found to be mid-way between source and electrode.

In one particular device in accordance with the invention, the following combination of dimensions and operating parameters were found to give optimum results for the detection of TEP vapour in air:

Internal diameter of cell body and ionising source holder: 10 mm
Spacing between ionising source and collector electrode: 14 mm
Spacing between ionising source and grid: 7 mm
Air flow rate: 1.5 l/min
Grid voltage: +19 V
Collector electrode voltage: −1.5 V
All other components earthed
Ionising source: Alpha-emitting (5.5 meV)
Americium 241 foil, strength 1.5 μCi Under these operating conditions, the ion current when sampling clean air was between 30 and 40 pA. When a dust filter was used, the background noise fluctuation was only ±2 pA, but when it was removed the fluctuation increased to ±10 pA.

The response curve obtained when sampling air containing a varying proportion of TEP vapour is shown in FIG. 2. The response values represent the change in ion current (plotted to a linear scale) obtained for various concentrations of TEP vapour in air (plotted to a logarithmic scale).

As may be seen, a very sensitive indication of impurity level is obtained.

I claim:

1. A method of monitoring polar vapours in a gas comprising the steps of:
   passing a continuous stream of gas through a passage;
   ionizing said stream in a region of said passage so that any polar vapours present will react with the gas ions formed to generate ion clusters; and
   collecting ions carried downstream by said gas stream at a location so that no substantial number of the gas ions remain in said stream while a substantial proportion of the ion clusters remain in said stream.

2. A method as in claim 1 including the further step of removing uncombined gas ions from said stream between the location of ionizing and the location of collecting.

3. A method as in claim 2 wherein said step of removing includes the step of applying an electrostatic field to said stream with the lines of force transverse to the direction of flow of said stream.

4. Apparatus for monitoring for polar vapours in a gas comprising:

a body member defining a passage through which a continuous stream of the gas may pass;

means for inducing a continuous flow of gas through said passage;

an ionizing source associated with a region of said passage such that ionization of the gas stream takes place substantially only within said region and also any polar vapour molecules present therein will react with the gas ions formed to generate ion clusters; and a collector electrode for collecting ions carried by the gas stream, said electrode being positioned in said passage downstream of said region and separated therefrom by a distance which is sufficient to ensure that no substantial number of the gas ions formed in said region remain in the gas stream at the collector electrode whilst ensuring that a substantial proportion of the ion clusters formed in said region remain in the gas stream at the collector electrode.

5. Apparatus according to claim 4 and further comprising means for enhancing the removal of uncombined gas ions from the gas stream between the ionizing source and the collector electrode whilst permitting ion clusters formed on polar molecules to remain therein.

6. Apparatus according to claim 4 wherein the ionizing source is a radioactive alpha-source, and a baffle is present in the passage downstream of the radioactive source for confining the region in which ionization can take place whilst permitting the flow of gas therepast.

7. Apparatus according to claim 4 wherein the collector electrode comprises a wire mesh screen extending transversely across the passage.

8. Apparatus according to claim 5 wherein the means for enhancing comprises means for applying, at a location between the ionising source and the collector electrode, an electrostatic field in which the lines of force are transverse to the direction of gas flow through the passage.

9. Apparatus according to claim 8 wherein the means for applying an electrostatic field comprises a grid of substantially parallel wires extending transversely across the passage at a location between the ionising source and the collector electrode.

10. Apparatus according to claim 6 wherein the radioactive alpha-source comprises americium 241.

11. Apparatus according to claim 10 wherein the radioactive alpha-source is in the form of a foil formed to the interior surface of the passage so as completely to surround the gas flow therethrough.

12. Apparatus according to claim 6 wherein the baffle comprises an overlapping plate and annulus spaced apart longitudinally of the passage, the cross-section of the plate being larger than the inner cross-section of the annulus.

13. Apparatus according to claim 4 comprising a filter through which gas must pass before entering the passage.

14. Apparatus according to claim 13 wherein the filter comprises polypropylene.

15. Apparatus according to claim 13 wherein the filter comprises polytetrafluoroethylene.

16. Apparatus according to claim 4 comprising a pump connected downstream of the collector electrode whereby the gas stream may be drawn through the passage.

17. Apparatus according to claim 4 wherein the internal surface of the passage upstream of the ionising source is of relatively non-absorbent material.

18. Apparatus according to claim 17 wherein the relatively non-adsorbent material is polytetrafluoroethylene.

19. Apparatus according to claim 4 comprising a screen of conductive material surrounding the passage between the ionising source and the collector electrode.

* * * * *